(12) United States Patent
Marie et al.

(10) Patent No.: US 11,998,751 B2
(45) Date of Patent: Jun. 4, 2024

(54) METHOD AND DEVICE FOR PROCESSING A CARDIAC SIGNAL

(71) Applicant: SORIN CRM SAS, Clamart (FR)

(72) Inventors: Elodie Marie, Vienne en Bessin (FR); Luca Vitali, Strambino (IT)

(73) Assignee: SORIN CRM SAS, Clamart (FR)

( * ) Notice: Subject to any disclaimer, the term of this patent is extended or adjusted under 35 U.S.C. 154(b) by 222 days.

(21) Appl. No.: 17/110,904

(22) Filed: Dec. 3, 2020

(65) Prior Publication Data

US 2021/0170183 A1 Jun. 10, 2021

(30) Foreign Application Priority Data

Dec. 4, 2019 (FR) ...................................... 1913710

(51) Int. Cl.
| | |
|---|---|
| *A61B 5/00* | (2006.01) |
| *A61B 5/287* | (2021.01) |
| *A61B 5/29* | (2021.01) |
| *A61B 5/318* | (2021.01) |
| *A61N 1/00* | (2006.01) |
| *A61N 1/37* | (2006.01) |

(52) U.S. Cl.
CPC ............ *A61N 1/3712* (2013.01); *A61B 5/287* (2021.01); *A61B 5/29* (2021.01); *A61B 5/318* (2021.01)

(58) Field of Classification Search
CPC ...................................................... A61B 5/318
See application file for complete search history.

(56) References Cited

U.S. PATENT DOCUMENTS

| | | |
|---|---|---|
| 5,447,518 A | 9/1995 | Pless |
| 5,513,644 A | 5/1996 | McClure et al. |
| | (Continued) | |

FOREIGN PATENT DOCUMENTS

| | | |
|---|---|---|
| EP | 2 407 097 A1 | 1/2012 |
| JP | H06205847 A | 7/1994 |
| | (Continued) | |

OTHER PUBLICATIONS

France Search Report on French Application No. 1913710 dated Nov. 12, 2020.

*Primary Examiner* — John R Downey
*Assistant Examiner* — Anant A Gupta

(57) ABSTRACT

A method for processing a cardiac signal represented as a function of time includes providing a number n of different threshold levels $N_i$, with i=1 to n and n being greater than or equal to three; detecting, from a given time T and per threshold level $N_i$, at least two successive intersections of the cardiac signal with the threshold level $N_i$, considering a crossing per increasing and/or decreasing value of the cardiac signal with the threshold level $N_i$; and determining at least one statistical parameter for the cardiac signal from the intersections of the cardiac signal with the at least three different threshold levels $N_i$. The method may be implemented by a subcutaneous active implantable medical device having a control circuit configured to process a cardiac signal.

18 Claims, 8 Drawing Sheets

(56) References Cited

U.S. PATENT DOCUMENTS

| | | | |
|---|---|---|---|
| 2007/0078488 A1 | 4/2007 | Bjorling et al. | |
| 2012/0016249 A1* | 1/2012 | Lian .................. | A61B 5/349 |
| | | | 600/509 |
| 2013/0035739 A1 | 2/2013 | Goto | |
| 2014/0142395 A1* | 5/2014 | Sattler ................ | A61B 5/725 |
| | | | 128/204.23 |

FOREIGN PATENT DOCUMENTS

| | | | |
|---|---|---|---|
| JP | 2001346771 A | 12/2001 |
| JP | 2003225218 A | 8/2003 |
| JP | 2005080712 A | 3/2005 |
| JP | 2008538989 A | 11/2008 |
| JP | 2013031571 A | 2/2013 |
| WO | 2006115778 A2 | 11/2006 |

* cited by examiner

METHOD AND DEVICE FOR PROCESSING A CARDIAC SIGNAL

CROSS-REFERENCE TO RELATED PATENT APPLICATIONS

This application claims the benefit of and priority to French Patent Application No. 1913710, filed Dec. 4, 2019, which is incorporated by reference herein in its entirety.

BACKGROUND

The present invention relates to a device and to its method for processing a signal originating from the heart, in particular an implantable cardiac defibrillator with a subcutaneous lead.

The rapid and reliable detection of cardiac arrhythmias is the key to the function of a defibrillator. Delayed or missing shocks could be fatal for a patient suffering from ventricular fibrillation as well as for other types of unstable haemodynamic arrhythmia (i.e. in which the heart does not generate circulation of the blood). At the same time, shocks without purpose should be avoided because they are generally associated with a number of undesirable effects.

In order to detect arrhythmic events, defibrillators generally examine the electrical signals generated by the heart and interpret these signals in order to determine the cardiac rhythm. When the cardiac rhythm deviates from normality and fulfils certain criteria (for example it is faster than a predetermined rhythm), tachycardia is assumed to have been detected and a shock can be delivered to the patient.

A key factor in determining the cardiac rhythm is the ability to differentiate the QRS complex, as illustrated in FIG. 1a, which marks the start of ventricular contraction, from the other components of the electrical cardiac signal, in particular the T wave and the P wave. If the device is capable of detecting all the QRS complexes and only the QRS complexes, reliable detection of the rhythm can be carried out.

However, reliably detecting the cardiac rhythm proves to be more complicated in a subcutaneous defibrillator than in a conventional endocardial (i.e. intracavitary) defibrillator. In fact, in an endocardial defibrillator, the electrical signals tend to have a more favourable morphology for detecting the cardiac rhythm than in a subcutaneous defibrillator. This results, inter alia, from the fact that with a lead implanted in the right ventricle, the largest component of the signal is the depolarisation potential, which is represented by the QRS complex illustrated in FIG. 1a; while the T wave and the P wave are almost absent or can be effectively distinguished by an appropriate high pass filter or band pass filter.

In a subcutaneous defibrillator, the cardiac signals detected by the electrodes located on the subcutaneous lead more closely resemble those of a standard surface electrocardiogram (ECG) in which all of the components are present, sometimes with morphological characteristics and amplitudes which make it difficult to detect the cardiac rhythm consistently.

The methods for detecting cardiac rhythm which are currently used are based on characteristic processing steps. A first step generally consists of amplifying and filtering the input ECG signal, with the aim of improving the desired components and removing the less important components. However, unsuitable or aggressive filtering could result in losing components which are useful for the detection of the cardiac rhythm.

Typically, the pre-processed signal is then compared with a predetermined threshold; one cycle is counted when the threshold is crossed. Counting of the cycle is usually inhibited during a short period, termed the refractory period, after detecting that a threshold has been crossed in order to avoid redundant counting of the same cycle, for example. An example of redundant counting of the cycle is illustrated in FIG. 1b. This counting error is often encountered in subcutaneous defibrillators and, as is shown in the example illustrated in FIG. 1b, may be caused by the incorrect detection of the T wave in a cardiac cycle (in addition to the detection of the QRS complex). When this phenomenon occurs, each cardiac cycle is counted twice, the consequence being an apparent doubling of the heart rate, which could result in a false detection of tachycardia and inappropriate shock delivery.

As illustrated in FIG. 1b, many methods for detection of the cardiac rhythm are linked to a comparison of the pre-processed signal (amplification, filtering, etc.) with a single threshold level. A consequence of this "single threshold" approach is that it is essential that the threshold is always positioned correctly with respect to the characteristics of the signal, in order to be able to count the cardiac cycles correctly. In fact, a threshold which is positioned too high up, for example higher than the highest peaks of the signal, would never be crossed; in this case, the system would not detect any cardiac cycles, even though they were physiologically present. This case is known as "underdetection", which leads to incorrect detection of the cardiac rhythm. If, in contrast, the threshold is positioned at a level which is too low, as in the example of FIG. 1b, not only could it be crossed by the peaks of the QRS complex, but it could also be crossed by other components (in FIG. 1b, it is the T wave), thereby generating the conditions for multiple counting of the same cycle.

In order to overcome the difficulties linked to suitable positioning of the threshold, varying the level of the threshold in accordance with a scheme based, for example, on the amplitude of the highest peaks of the signal is known, as is illustrated in FIG. 1c. In this manner, the threshold is guaranteed to be as far as possible from the noise and unwanted complexes, which normally have a lower amplitude (see the four complexes b1, b2, b3, b4 in FIG. 1c).

However, it turns out that this approach is not very robust in respect of rapid changes in amplitude, as illustrated in FIG. 1c where the five peaks indicated by the arrows m1, m2, m3, m4, m5 are missed because they are masked by the four higher preceding peaks (see e1, e2, e3, e4 in FIG. 1c) which have resulted in raising the threshold level for detection, well beyond the amplitude of peaks m1 to m5.

In addition, implementing the methods as described below for filtering the input signal and implementing a detection method by crossing the detection threshold leads to complex algorithms and costly software resources (digital processing).

With the aim of overcoming the limitations set out above, the present invention aims to improve the reliability and robustness of processing a cardiac signal, in particular a signal captured by a subcutaneous lead, while minimising the input signal filtering steps and cost of software resources.

The aim of the present invention is achieved by means of a method for processing a cardiac signal represented as a function of time, comprising the steps of: a) providing a number n of different threshold levels $N_i$, with i=1 to n and n being greater than or equal to three; b) detecting, from a given time T and per threshold level $N_i$, at least two successive intersections of the cardiac signal with the threshold level $N_i$, considering a crossing per increasing and/or decreasing value of the cardiac signal with the threshold level $N_i$; and c) determining at least one statistical parameter for the cardiac signal from the intersections of the cardiac signal with the at least three different threshold levels $N_i$.

Thus, instead of depending on a single threshold which is fixed or changes over time as described above in respect of known methods, in the present method at least three different, separated, threshold levels are considered at the same time. The signal is thus compared simultaneously to all of the thresholds, which means that a threshold crossing model can be obtained which is based on the intersections of the cardiac signal with the various threshold levels. In addition, this method does not require discrimination by filtering. By eliminating discrimination by filtering, all of the information present in the signal is preserved and can be exploited. This is particularly advantageous when differences in morphology, amplitude, and frequency between the desired and undesired components are subtle and it is important to preserve every element of the information in order to carry out processing of the cardiac signal.

SUMMARY

The present invention, which relates to a method for processing a cardiac signal, may be further improved by means of the following embodiments.

In accordance with one embodiment, the determination of at least one statistical parameter in step c) may comprise the determination of a period of the cardiac signal.

Thus, the various intersections of the cardiac signal with the threshold levels together contribute to the determination of a period for the cardiac signal, i.e. not only the peaks of the QRS complex, but also the T wave or even the P wave, which are generally filtered out as much as possible for known methods so that they are not detected.

In accordance with one embodiment, step b) may further comprise the determination, from the given time T and per threshold level $N_i$, of at least one elapsed time $\Delta_1 t_i$, i=1 to n, between two successive intersections of the cardiac signal with the threshold level $N_i$; and such that the at least one statistical parameter may be determined in step c) by means of the elapsed times $\Delta_1 t_i$ determined in step b) from the given time T.

Thus, the method does not require complex calculations in order to determine the statistical parameter, which means that the calculations can be simplified and software resource costs can be reduced.

In accordance with one embodiment, a first elapsed time $\Delta_1 t_i$ may be determined per threshold level $N_i$ between the two most recent successive intersections from the given time T; and a second elapsed time $\Delta_2 t_i$ may be determined per threshold level $N_i$ between the most recent intersection and the third most recent intersection from the given time T; step c) further comprising the determination of at least one statistical parameter for the cardiac signal by comparing the first elapsed times $\Delta_1 t_i$ with the second elapsed times $\Delta_2 t_i$.

Thus, the method is further characterized by an approach which is rather more "stochastic" than "deterministic", as was the case with previous known methods. In the other known methods, periodic and precise crossings of the "deterministic" type with a single threshold are necessary because each crossing supplies complete information on the end of a cardiac cycle and the start of another. In contrast, in the present method in accordance with the invention, each intersection (i.e. crossing of one of the thresholds by the signal) contributes to the determination of the statistical parameter, and no one intersection is more important than the others. In addition, the characteristics of the cardiac signals are typically such that for the majority of threshold crossings, the elapsed time $\Delta_1 t_i$ and/or the elapsed time $\Delta_2 t_i$ is close to the period which is being determined, i.e. the cardiac rhythm.

In accordance with one embodiment, in step c), the period of the cardiac signal from the given time T may be determined from the distribution by number of the elapsed times $\Delta_1 t_i$; $\Delta_2 t_i$ which, in particular, is represented by means of a histogram.

Thus, the method does not require complex calculations in order to determine the statistical parameter, which means that calculations can be simplified and software resource costs can be reduced, because in the distribution, for example represented by a histogram, it is the time which has elapsed, $\Delta_1 t_i$; or $\Delta_2 t_i$, which has been observed the most which corresponds to the value for the period of the cardiac signal, i.e. the cardiac rhythm.

In fact, similar duration values tend to converge about a common value, accumulating and giving rise to a higher bar for this duration in the histogram. Thus, this means that the period of the signal is readily legible from the histogram, even when small amplitude components are present and are taken into account.

In addition, changes in the distribution of the durations in the histogram may be an indication of the onset of arrhythmia, because the distribution of the duration values changes rapidly, and in particular, the maximum is reduced.

In accordance with one embodiment, the distribution by number of the elapsed times ($\Delta_1 t_i$; $\Delta_2 t_i$) per defined time interval may be represented by means of a histogram and the period of the cardiac signal from the given time T may be determined from a mean or a median of the elapsed times ($\Delta_1 t_i$; $\Delta_2 t_i$) comprised in the bar of the histogram which comprises the largest number of occurrences of the elapsed times ($\Delta_1 t_i$; $\Delta_2 t_i$).

Thus, it is possible to determine, in a more precise manner, the duration of the period of the most frequent cardiac signal which is within the interval of said bar of the histogram.

In accordance with one embodiment, the distribution by number of the elapsed times ($\Delta_1 t_i$; $\Delta_2 t_i$) per defined time interval may be represented by means of a histogram and wherein the period of the cardiac signal from the given time T may be determined from a mean or a median of the elapsed times ($\Delta_1 t_i$; $\Delta_2 t_i$) comprised in a defined time interval which is greater than a time interval corresponding to that of one bar of the histogram.

Thus, it is possible to determine, in a more precise manner, the duration of the period of the cardiac signal which is the most frequent by considering the elapsed times both within the interval of one bar of the histogram and outside the bar of the histogram, defined by the defined interval.

In accordance with one embodiment, in step c) only the elapsed times ($\Delta_1 t_i$; $\Delta_2 t_i$) for which the value crosses a predefined threshold may be taken into account in the determination of the at least one statistical parameter.

Thus, the predefined threshold can be used to guarantee the robustness of the method.

In accordance with one embodiment, the predefined threshold may be determined from the detection of successive intersections of the cardiac signal with the threshold level $N_i$, at a time before the given time T.

Thus, a supplemental step for detection and calculation is not necessary in order to determine the predefined threshold. The present method is thus further optimised.

In accordance with one embodiment, step a) may comprise the determination of a minimum amplitude and of a maximum amplitude of the cardiac signal, so that the values for the different threshold levels $N_i$ may be determined so that they are comprised between a minimum value and a maximum value respectively corresponding to the minimum amplitude and the maximum amplitude of said signal.

Thus, the different threshold levels $N_i$ are determined in a manner such as to ensure the robustness of the method.

In accordance with one embodiment, the value for each of the different threshold levels $N_i$ may be constant over time.

Thus, the present method does not require the need for the threshold levels to be adapted continuously as a function of time, as is the case for known prior art methods. For this reason, the computing costs can be reduced and the method is simplified.

In accordance with one embodiment, the value for the different threshold levels $N_i$ may vary over time as a function of the at least one statistical parameter.

Thus, the different threshold levels $N_i$ may advantageously be adapted as a function of the time of day (sleep phase, active phase) and/or over the lifetime of the patient.

In accordance with one embodiment, the different threshold levels $N_i$ may be spaced apart from each other by a fixed interval.

Thus, the various threshold levels $N_i$ may be positioned advantageously for a cardiac signal in a manner such as to further improve the robustness of the method.

In accordance with one embodiment, step a) may comprise the determination of at least ten different threshold levels $N_i$.

Because each threshold crossing makes a contribution in the present method, the more thresholds there are, the better is the determination of the statistical parameter for the cardiac signal. Thus, the presence of at least ten different threshold levels $N_i$ means that the robustness of the method, in particular for detecting variations in amplitude of the signal, can be further improved.

In accordance with one embodiment, each of the threshold levels $N_i$ may be different from a base line.

The base line may be crossed several times as a function of time, even without a signal, because of the presence of noise which is intrinsic to each system. Crossing of a threshold with a level of zero, i.e. the base line, could be affected by noise whether the signal is absent or present. For this reason, the base line is advantageously omitted from the various threshold levels $N_i$ of the method in accordance with the present invention.

In accordance with one embodiment, the method may further comprise a step for receiving at least one cardiac signal via an implantable lead of an active implantable medical device which is configured to capture a cardiac signal subcutaneously.

Thus, the method is configured to process a subcutaneously captured cardiac signal. In effect, the method is adapted for processing a cardiac signal of this type for which all components are present—QRS complex. P wave and T wave. For this reason, the method is configured for the determination of the morphological and amplitude characteristics of a subcutaneously captured cardiac signal.

In accordance with one embodiment, the method may further comprise a step for determining an interval between crossings of two successive threshold levels $N_i=n$ and $N_i=n+1$ by the cardiac signal.

Thus, a value is obtained which is similar to a derivative of the cardiac signal, which means that two events of the same intensity but different morphologies can be distinguished, such as a peak of the QRS complex from an artefact.

The aim of the present invention is also achieved by means of a subcutaneous active implantable medical device comprising: a housing; an implantable subcutaneous lead connected to the housing; the subcutaneous implantable lead comprising one or more sensing electrodes configured to capture cardiac signals subcutaneously; the device further comprising a control circuit configured to carry out the method for processing a cardiac signal from at least one of cardiac signals captured by the subcutaneous lead.

BRIEF DESCRIPTION OF THE DRAWINGS

The invention and its advantages will now be explained in more detail below by means of preferred embodiments, in particular made with reference to the accompanying figures, in which:

FIG. 5b represents an enlargement of the third histogram illustrated in FIG. 5a;

DETAILED DESCRIPTION

The invention will now be described in more detail using advantageous embodiments by way of example and with reference to the drawings. The embodiments described are simply configurations which are possible and it should be borne in mind that the individual features as described above may be provided independently of each other or may be omitted altogether when carrying out the present invention.

Figure 1A:
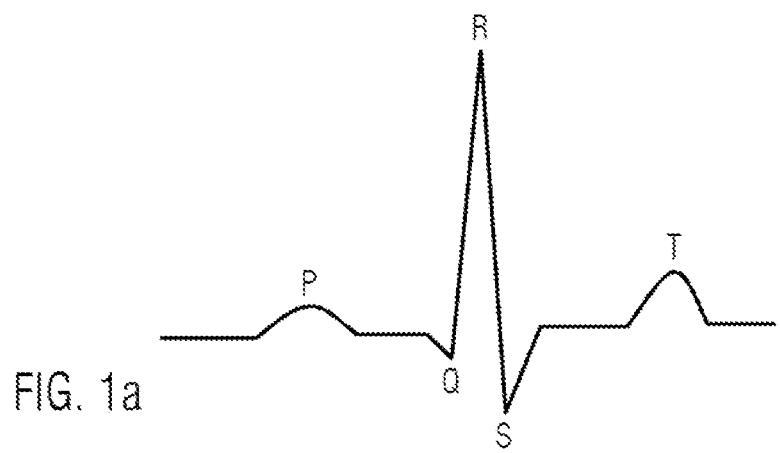
FIG. 1a represents a standard trace for a QRS complex.
Figure 1B:
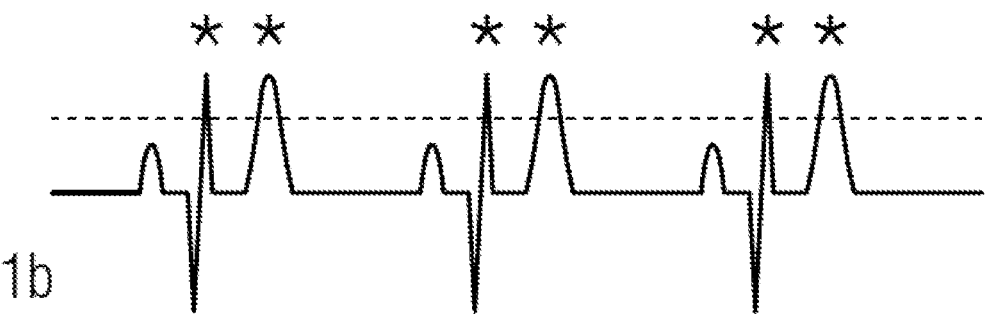
FIG. 1b represents a cardiac signal and a constant threshold in accordance with a known prior art method.
Figure 1C:
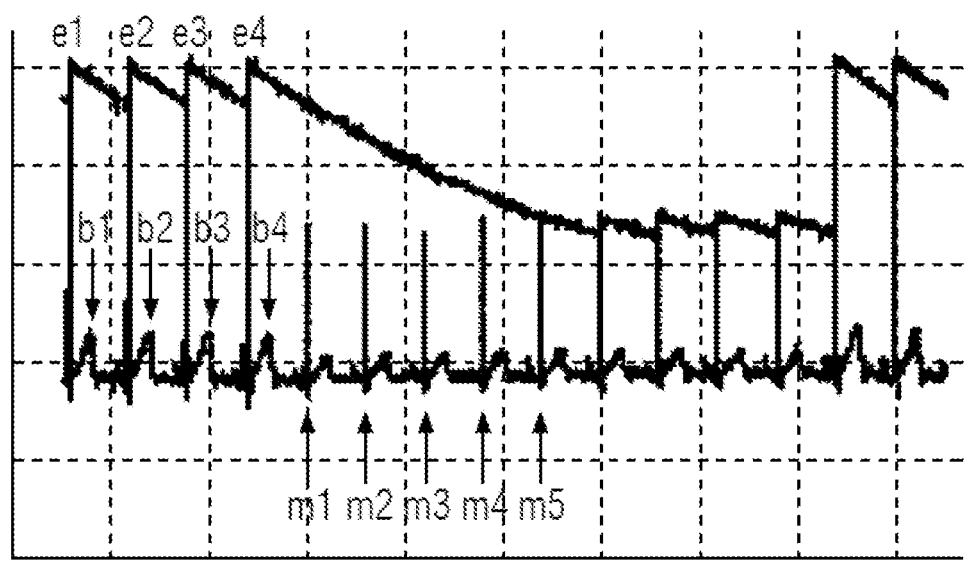
FIG. 1c represents a cardiac signal and a variable threshold in accordance with a known prior art method.
Figure 2:
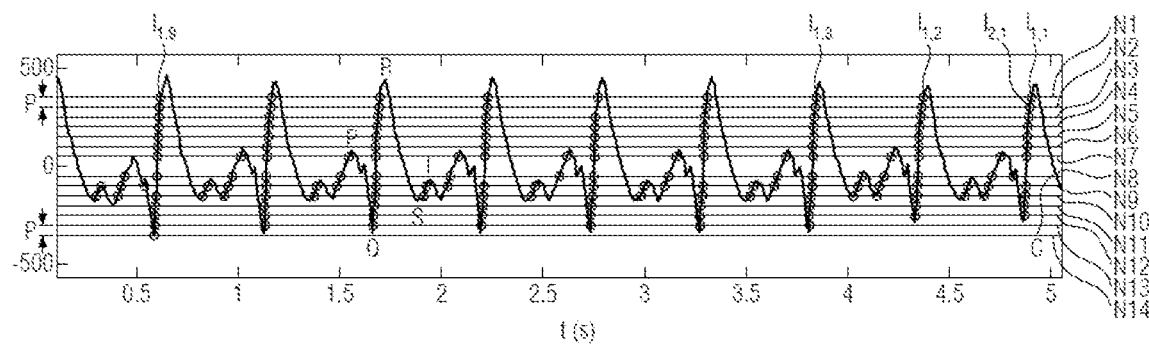
FIG. 2 represents a cardiac signal and a plurality of thresholds in accordance with the method of the present invention.

The trace C of FIG. 2 represents a cardiac signal of an electrocardiogram (ECG) as a function of time.

The horizontal lines, parallel to the abscissa, i.e. to the time axis, represent a plurality of threshold levels $N_i$, with i=1 to 14 in the example of FIG. 2. In accordance with the present invention, the number of threshold levels $N_i$ may vary, while remaining greater than or equal to 3. It should be noted that the more threshold levels $N_i$ there are, the better will be the determination of a statistical parameter for the cardiac signal. Thus, taking more threshold levels $N_i$ into account means that the robustness of the method, in particular for detecting the variations in amplitude of the cardiac signal, can be improved.

Each of the circles in FIG. 2 represents crossing of a certain threshold level $N_i$ by the cardiac signal in the upwards direction, i.e. by the increasing value of the cardiac signal. Thus, each circle corresponds to a point of intersection $I_{i,j}$ between the cardiac signal and a threshold level $N_i$, with i=1 to 14 and j=1 to 9 in the example of FIG. 2.

In a variation, crossing of each threshold level by the cardiac signal may be considered in the downwards direction, i.e. by a decreasing value of the cardiac signal.

In another variation, crossing of the threshold levels $N_i$ by the cardiac signal in the two directions (upwards and downwards) may be envisaged simultaneously.

In the example illustrated in FIG. 2, the threshold level corresponding to the level zero has been deliberately omitted because it corresponds to the base line, which could be crossed several times over time, even without a signal, because of the noise intrinsic to each physical system. Thus, since the crossing of the zero level threshold could be affected by noise whether the signal is present or absent, the plurality of threshold levels $N_i$, with i=1 to 14 are deliberately other than zero.

In the example illustrated in FIG. 2, the value for each of the different threshold levels $N_i$ is constant over time. Thus, the present method does not require the threshold levels to be adjusted continuously as a function of time, as is the case with known prior art methods. For this reason, the cost of computations can be reduced and the method is simplified.

In a variation, the value for the different threshold levels $N_i$ may vary over time. Thus, the different threshold levels $N_i$ may advantageously be adapted to the time of day (sleep phase, active phase) and/or to the lifestyle of the patient.

In accordance with the example illustrated in FIG. 2, the threshold levels $N_i$ with i=1 to 7 and $N_i$ with i=8 to 14 are successively separated from each other by the same interval "p". It should be noted that the interval between the threshold levels $N_i$, i.e. the value of the interval "p", may be fixed or may change over time.

The different threshold levels $N_i$ may thus advantageously be positioned with respect to the cardiac signal in a manner such as to further improve the robustness of the method. In addition, the method of the present invention may comprise the determination of a minimum amplitude and of a maximum amplitude of the cardiac signal, so that the values for the different threshold levels $N_i$ are selected so that they are comprised between a minimum value and a maximum value respectively corresponding to the minimum amplitude and the maximum amplitude of said cardiac signal.

Thus, this ensures that over time, the cardiac signal will always cross at least a plurality of thresholds $N_i$. It should, however, be accepted that over time, the cardiac signal will not cross all of the thresholds $N_i$.

Figure 3:
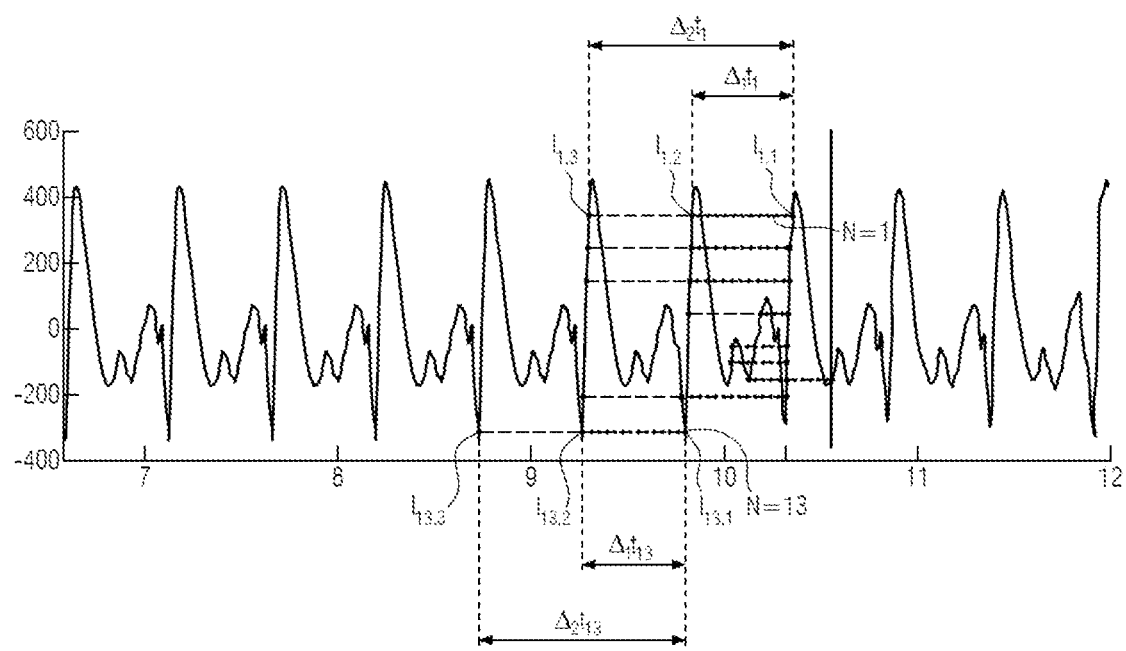
FIG. 3 represents a cardiac signal and a plurality of elapsed times in accordance with the method of the present invention.

In accordance with the present invention, the cardiac signal is simultaneously compared with all of the thresholds $N_i$, which means that a statistical model of crossing of the threshold can be obtained. An example of this method is illustrated in FIG. 3 and in FIGS. 4a, 4b and 4c.

The method in accordance with the present invention consists of providing a number n of different threshold levels $N_i$, with i=1 to n and n being greater than or equal to three, i.e. at least three different threshold levels $N_i$, as explained with reference to FIG. 2, and of detecting, from a given time T and per threshold level $N_i$, at least two successive intersections $I_{i,j}$ of the cardiac signal with the threshold level $N_i$, considering one crossing per increasing and/or decreasing value of the cardiac signal with the threshold level $N_i$.

For each threshold level $N_i$, with i=1 to n, a first elapsed time $\Delta_1 t_i$ is determined between two successive intersections $I_{i,j}$ and $I_{i,j+1}$ of the cardiac signal with the threshold level $N_i$. The first elapsed time $\Delta_1 t_i$ corresponds to the difference between the most recent crossing from the time T and the second most recent crossing with the same threshold level. In FIG. 3, the segment $\Delta_1 t_i$ represents the first elapsed time from the time T for the threshold level $N_1$ between the first intersection $I_{1,1}$ and the second intersection $I_{1,2}$ of the threshold $N_1$ with the signal. Similarly, the segment $\Delta_1 t_{13}$ represents the first elapsed time from the time T for the threshold level $N_{13}$ between the first intersection $I_{13,1}$ and the second intersection $I_{13,2}$ of the threshold $N_{13}$ with the signal.

In addition, for each threshold level $N_i$, with i=1 to n, a second elapsed time $\Delta_2 t_i$ is determined per threshold level $N_i$ between the most recent intersection $I_{i,j}$ and the most recent third intersection $I_{i,j+2}$ from the given time T. The second elapsed time $\Delta_2 t_i$ corresponds to the difference between the most recent crossing from the time T and the third most recent crossing for the same threshold level. In FIG. 3, the segment $\Delta_2 t_i$ represents the second elapsed time from the time T for the threshold level $N_i$ between the first intersection $I_{1,1}$ and the third intersection $I_{1,3}$ of the threshold $N_1$ with the signal. Similarly, the segment $\Delta_2 t_{13}$ represents the second elapsed time from the time T for the threshold level $N_{13}$ between the first intersection $I_{13,1}$ and the third intersection $I_{13,3}$ of the threshold $N_{13}$ with the signal.

The determination of at least one statistical parameter for the cardiac signal is obtained by comparing the first elapsed times $\Delta_1 t_i$ with the second elapsed times $\Delta_2 t_i$, by considering the plurality of threshold levels $N_i$ simultaneously.

It will be noted that a first duration $\Delta_1 t_i$ and a second duration $\Delta_2 t_i$ are determined for each threshold level $N_i$, even though these are not shown in FIG. 3 for reasons of clarity.

It will also be noted that the threshold level $N_{14}$ (illustrated in FIG. 2), corresponding to the lowest threshold, has deliberately been omitted from the representation of FIG. 3 because the cardiac signal does not cross the threshold $N_{14}$ in the window of time illustrated in FIG. 3. It turns out that the present method does not require that the signal should cross all of the thresholds $N_i$; this makes the method even more tolerant to variations in the amplitude of the signal compared with known methods based on a single threshold. Advantageously, the present method tolerates both slow variations and sudden variations in the amplitude of the cardiac signal, provided that the signal crosses a minimum number of thresholds, i.e. at least three, and in particular at least ten, so that certain information can be extracted from the signal, as will be explained below.

Figure 4A:
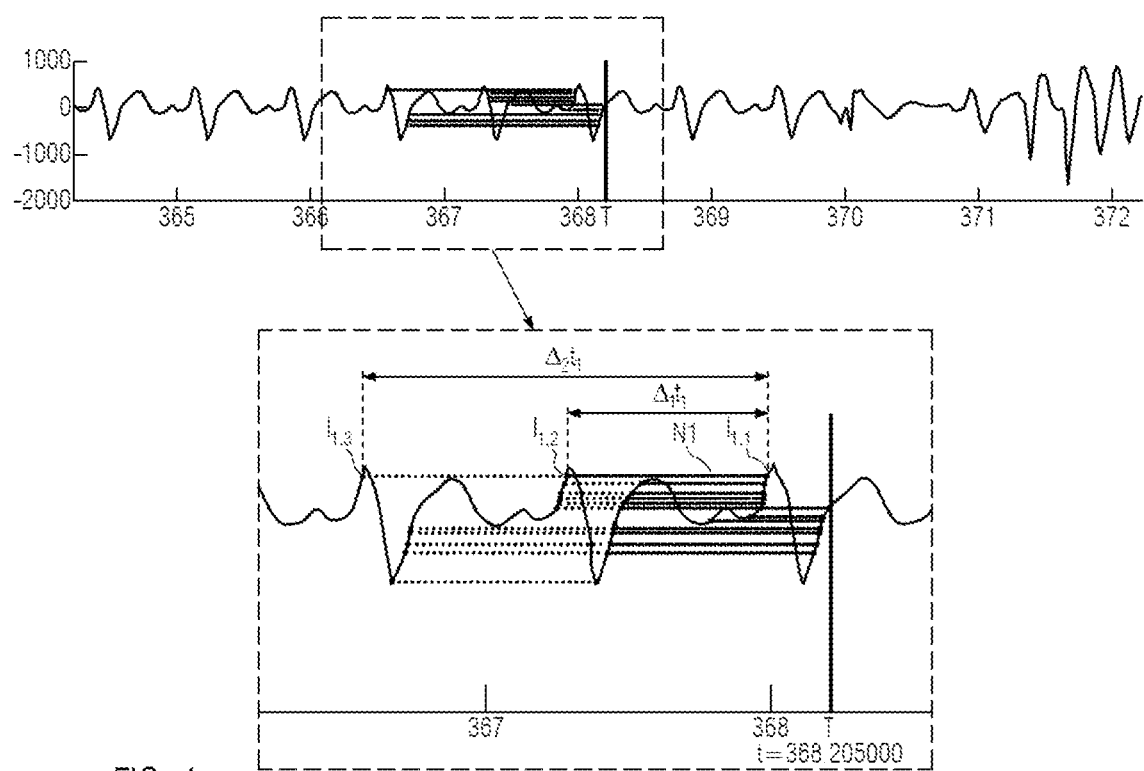
FIG. 4a represents a cardiac signal and a plurality of elapsed times in accordance with an example of the method of the present invention.
Figure 4B:
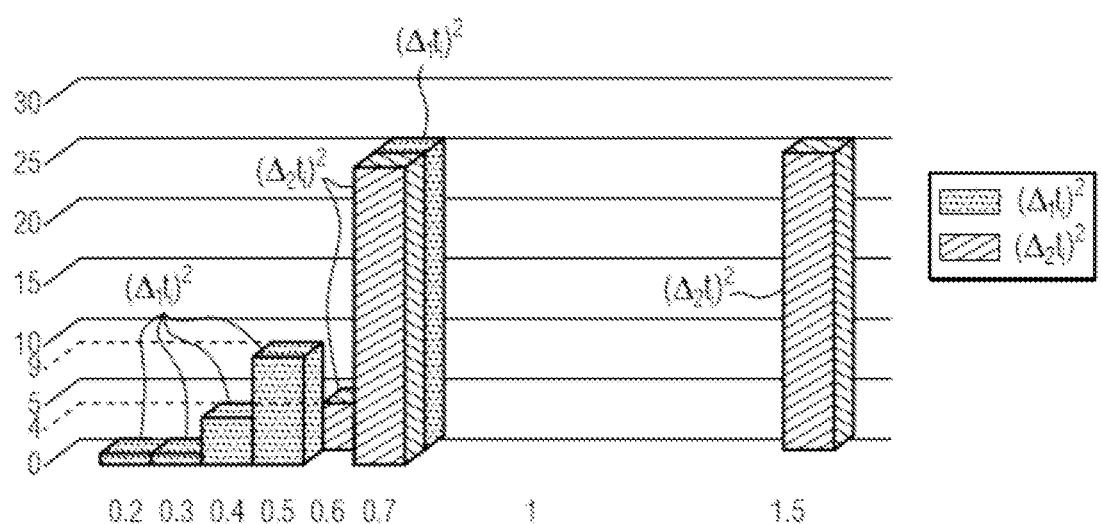
FIG. 4b represents a first histogram comprising the plurality of elapsed times determined from the cardiac signal of FIG. 4a of the method of the present invention.
Figure 4C:
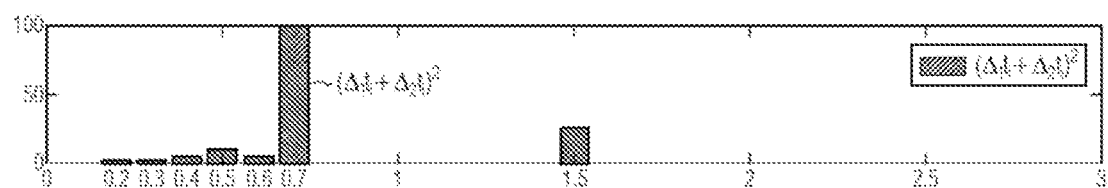
FIG. 4c represents a second histogram comprising the plurality of elapsed times determined from the cardiac signal of FIG. 4a of the method of the present invention.

FIGS. 4a, 4b and 4c represent successive steps of the method for processing a cardiac signal in accordance with the present invention. The elements with the same reference numerals which have already been used in FIGS. 2 and 3 will not be described again in detail, but reference should be made to their description above.

FIG. 4a represents a cardiac signal and threshold levels $N_i$ which cross the signal at a plurality of intersections $I_{i,j}$. As was explained with reference to FIG. 3, the method of the present invention comprises a step in which first elapsed times $\Delta_1 t_i$ and second elapsed times $\Delta_2 t_i$ are determined. For the purposes of clarity, only the elapsed times $\Delta_1 t_1$ and $\Delta_2 t_1$ have been shown for the first threshold level $N_1$ of FIG. 4a. It should be noted that the determination of the elapsed times for the other threshold levels $N_1$ is carried out in the same manner as that described in FIG. 3 to which reference is made, and will not be described again in detail.

In order to extract a statistical parameter from the cardiac signal, such as the period of the cardiac signal for determining the cardiac rhythm, for example, from information supplied by the set of durations $\Delta_1 t_i$ and $\Delta_2 t_i$, said durations $\Delta_1 t_i$ and $\Delta_2 t_i$ are represented graphically by means of a histogram.

FIG. 4b represents such a histogram which is shown in three dimensions, and in which the bars filled with dots correspond to the distribution of the observed numbers $N_{1,j}$ for the square of the first elapsed times $\Delta_1 t_i$ and the bars filled with oblique lines correspond to the distribution of the numbers $N_{2,j}$ for the square of the second elapsed times $\Delta_2 t_j$. The abscissa of the histogram of FIG. 4b represents the time intervals in seconds, while the ordinate of the histogram represents the number of occurrences of the elapsed times $\Delta_1 t_i$ and $\Delta_2 t_i$ observed in each of the time intervals.

It should be noted that the durations $\Delta_1 t_i$ and $\Delta_2 t_i$ which have not been updated for a long time, in particular beyond a predetermined duration, for example because of a reduction in the amplitude of the signal, are not taken into account in the histogram. In order to further highlight the elapsed times which appear most often in the cardiac signal, the number of occurrences of the elapsed times $\Delta_1 t_i$ and $\Delta_2 t_i$ is squared in the representation of the histogram.

In particular because of the inherent appearance of an electrocardiogram, a maximum appears in the histogram for a common value of elapsed times $\Delta_1 t_i$ and $\Delta_2 t_i$. The time interval for which the frequency of occurrence of the elapsed times $\Delta_1 t_i$ and $\Delta_2 t_i$ is the highest (i.e. the highest bar) may be considered to be the period of the cardiac signal which is to be detected. In the example illustrated in FIG. 4b, for the time interval centred on t=0.7 s, a majority of the occurrences of first elapsed times $\Delta_1 t_i$ and of second elapsed times $\Delta_2 t_i$ will be observed.

It will be observed that at the time interval centred on t=1.5 s, only an occurrence of second elapsed times $\Delta_2 t_i$ but no first elapsed times $\Delta_1 t_i$ are observed.

In FIG. 4c, the frequencies of occurrence of the elapsed times $\Delta_1 t_i$ and $\Delta_2 t_i$ have been added together then squared in order to make the histogram more legible, raising the highest bar even higher compared with the other bars of the histogram. This aspect is explained in more detail with the aid of Table 1 below.

Table 1 below represents the frequency of occurrence per time interval for the cardiac signal illustrated in FIG. 4a.

TABLE 1

| t | $\Delta_1 t_i$ | $(\Delta_1 t_i)^2$ | $\Delta_2 t_i$ | $(\Delta_2 t_i)^2$ | $\Delta_1 t_i + \Delta_2 t_i$ | $(\Delta_1 t_i + \Delta_2 t_i)^2$ |
|---|---|---|---|---|---|---|
| 0.2 | 1 | 1 | 0 | 0 | 1 | 1 |
| 0.3 | 1 | 1 | 0 | 0 | 1 | 1 |
| 0.4 | 2 | 4 | 0 | 0 | 2 | 4 |
| 0.5 | 3 | 9 | 0 | 0 | 3 | 9 |
| 0.6 | 0 | 0 | 2 | 4 | 2 | 4 |
| 0.7 | 5 | 25 | 5 | 25 | 10 | 100 |
| 1.5 | 0 | 0 | 5 | 25 | 5 | 25 |

The histogram of FIG. 4b represents the values $(\Delta_1 t_i)^2$ and $(\Delta_2 t_i)^2$ of Table 1, while the histogram of FIG. 4c represents the values $(\Delta_1 t_i + \Delta_2 t_i)^2$ from Table 1. The highest bar of the histogram of FIG. 4c therefore corresponds to the value 100. Thus, in accordance with the present method, a statistical method has been used to determine that the period of the cardiac signal represented in FIG. 4a corresponds to the duration indicated by the time interval for the histogram which is centered on t=0.7 s from the given time T.

In the example of FIG. 4c, it will be observed that the histogram highlights the correct value for the cardiac rhythm despite the presence of components with low amplitudes which are taken into account without in any way falsifying the result, because for the thresholds crossed by the low amplitude components, the value $\Delta_2 t_i$ indicates the suitable value of the refractory. For this reason, although the components with low amplitudes exist, they do not change whatsoever for the interpretation of the cardiac rhythm. Thus, the present method is even more tolerant of artefacts than known prior art methods.

It should be noted that each time interval of the histogram corresponds to a range of time values and is centred on a time value which is that indicated along the abscissa in FIGS. 4b and 4c. Thus, for example, the time interval centred on the value t=0.7 s of FIG. 4c corresponds to a range of time values in the range from t=0.65 s to t=0.75 s.

Figure 5A:
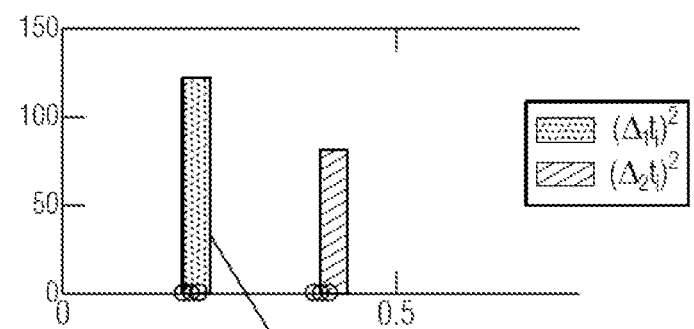
FIG. 5a represents a third histogram comprising a plurality of elapsed times determined from a cardiac signal in accordance with the method of the present invention.
Figure 5B:
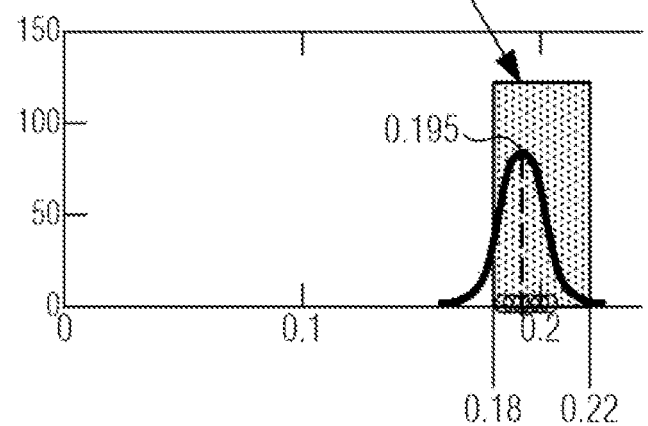

In accordance with a variation, it is possible to determine the duration of the most frequent period of the cardiac signal more precisely within a given range. FIG. 5a illustrates a histogram with a plurality of bars of elapsed times determined from a cardiac signal in accordance with the method of the present invention described above. FIG. 5b is an enlarged view of the highest bar of the histogram represented in FIG. 5a. It corresponds to an interval in the range from time values t=0.18 s to t=0.22 s and which is centred on the value t=0.20. FIG. 5b also illustrates the distribution of elapsed times within this range t=[0.18; 0.22]. Each of the respective time values for the elapsed times is indicated by a circle in FIG. 5b. A mean value for the elapsed times may be determined from this distribution. In a variation, a median of the elapsed times is what may be determined.

In the example illustrated in FIG. 5b, the mean of the elapsed times $\Delta_1 t_i$ in the time interval t=[0.18; 0.22] centred on the value t=0.20 s has the value t=0.195 s.

In a variation, the mean of the elapsed times is determined over a wider range of values than one defined time interval by the width of one bar of the histogram. Crossing of the thresholds $N_i$ by the cardiac signal may also be used to determine an interval between crosses of the thresholds of two successive thresholds $N_{i=n}$ and $N_{i=n+1}$. Thus, a value similar to a derivative of the cardiac signal is obtained which can be used to distinguish two events of the same intensity but different morphologies, as explained below with reference to FIG. 6 which shows the plots A and B.

The plot A represents a cardiac signal, in particular a rectified cardiac signal 11, comprising two peaks indicated by reference numerals 13 and 15. Plot A also illustrates four threshold levels $N_1$, $N_2$, $N_3$, $N_4$.

Plot B represents the time (indicated by each vertical line on plot B) at which the rectified cardiac signal 11 crosses one of the threshold levels $N_1$ to $N_4$.

A time interval 17 is defined between successive crossings by the peak 13 of the threshold level $N_1$ and the next threshold level, i.e. the threshold level $N_2$. Similarly, a time interval 19 is defined between crossings by the peak 15 of the threshold level $N_1$ and the threshold level $N_2$. In the same manner, a plurality of time intervals is defined for crossings by the peaks 13 and 15 of the remainder of the threshold levels Ni.

Figure 6:
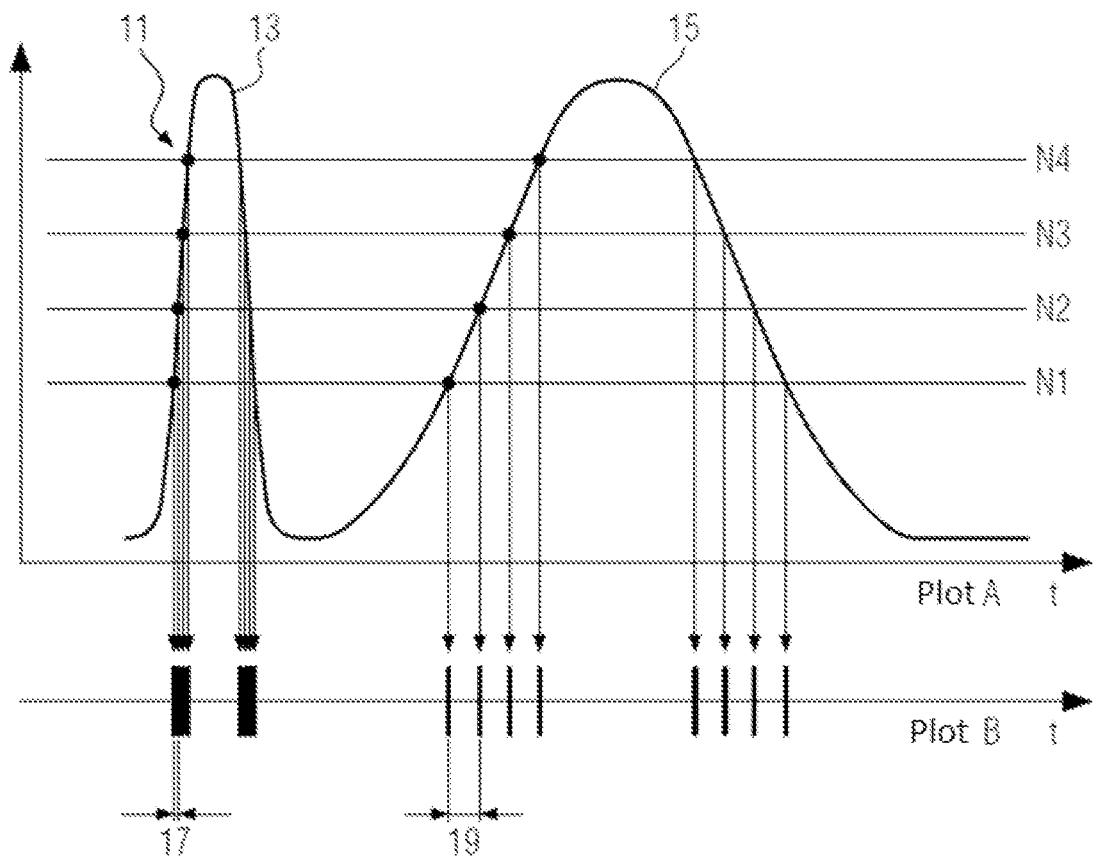
FIG. 6 represents two plots determined in order to discriminate an artefact from the cardiac signal in accordance with the present invention.

As illustrated in plot B of FIG. 6, the time intervals between two crossings of threshold levels relating to peak 13 are shorter than the time intervals between two crossings of threshold levels relating to the peak 15. It will be observed that the time interval 17 is shorter than the time interval 19.

From the information provided by the time intervals 17, 19 as illustrated in plot B, it then becomes possible to distinguish two different types of peaks of the cardiac signal, in particular in order to differentiate a peak relating to the cardiac rhythm (such as the peak 13 of plot A) from a peak generated by an artefact (such as the peak 15 of plot A).

In addition, because a plurality of threshold levels $N_j$ are considered simultaneously, the present method is adapted to the detection of a cardiac rhythm during a ventricular fibrillation, because the processing method has been shown to be even more robust and reliable and less dependent on particular events such as artefacts, for example. This aspect is described further and illustrated below with the aid of FIGS. 7a to 7d.

FIGS. 7a to 7d illustrate the manner in which the present method reacts during a transition from a normal sinus rhythm to an episode of ventricular fibrillation (also abbreviated to "VF" below). Each FIG. 7 represents a cardiac signal and two corresponding histograms, determined in the same manner as in FIGS. 4b and 4c.

Figure 7A:
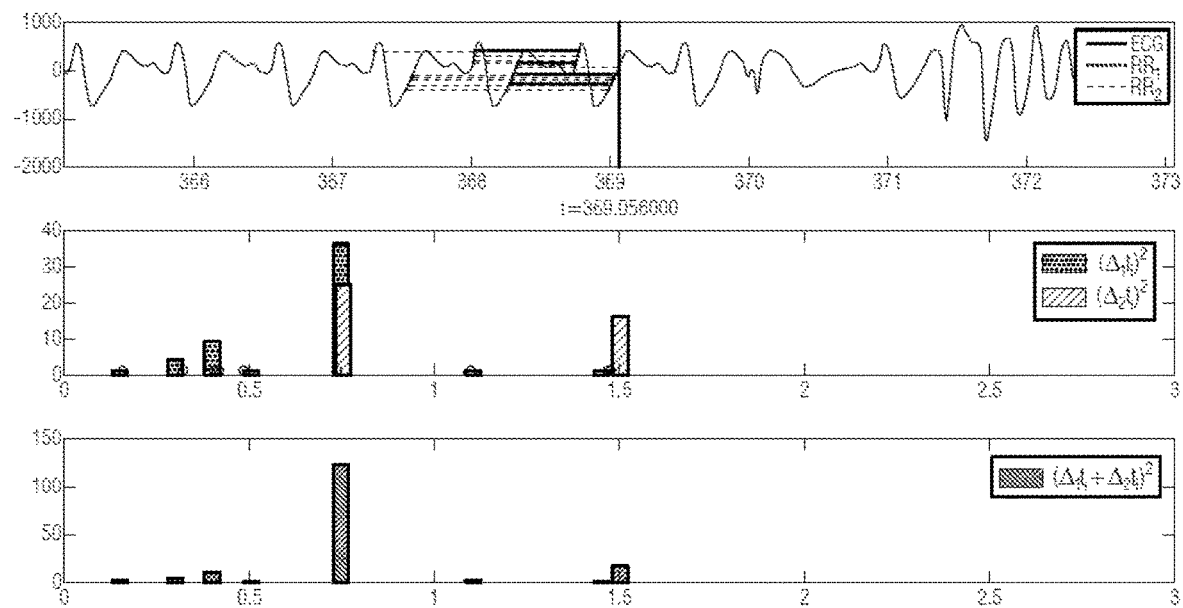
FIG. 7a represents a cardiac signal and corresponding histograms for the normal sinus rhythm.
Figure 7B:
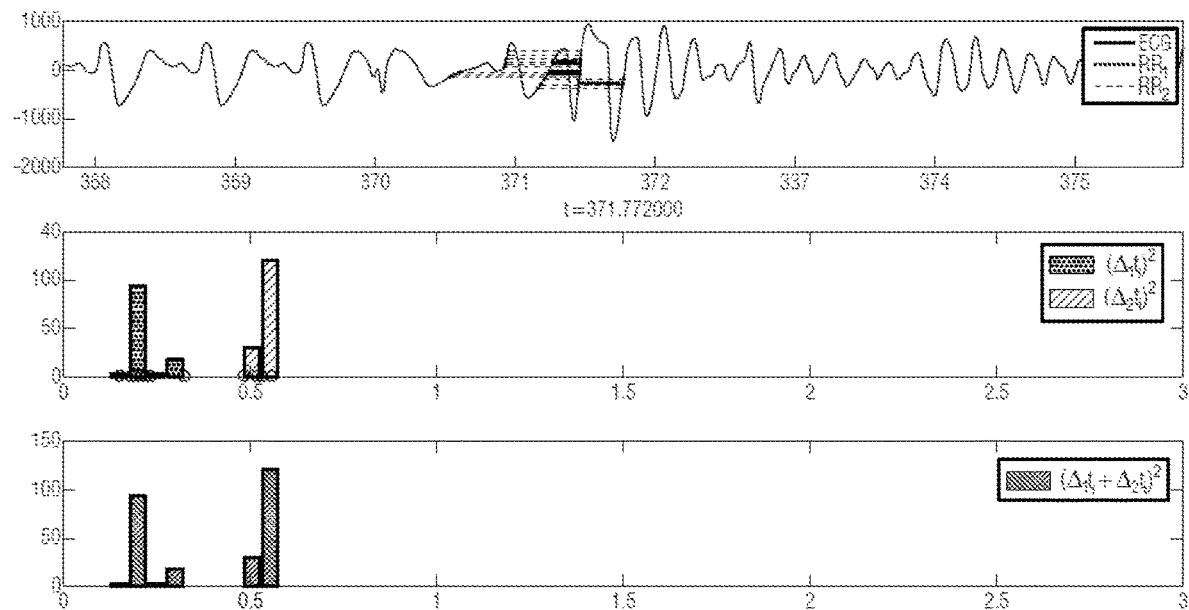
FIG. 7b represents a cardiac signal and corresponding histograms at the approach to a ventricular fibrillation episode.

FIG. 7a illustrates a normal sinus rhythm for which the present method can be used to determine that the predominant duration for the cardiac cycle period, as indicated by the histogram, corresponds to the highest bar the interval for which is centred on the value t=0.7 s. As a ventricular fibrillation approaches, an acceleration of the cardiac rhythm is already perceptible using the present method. In fact, as can be seen in FIG. 7b, as soon as a VF period begins, the histogram starts to become more dispersed, indicating "turbulence" in the cardiac rhythm. However, the cardiac rhythm is still relatively slow, with a predominant duration represented by the histogram of FIG. 7b at t=0.55 s.

A ventricular fibrillation generally starts as a salvo of rapid and regular ventricular tachycardia which then fragments into multiple wavelets. The sudden reduction in the amplitude of the cardiac signal just before and/or as soon as the VF episode begins is a typical phenomenon which is routinely observed. However, with the conventional approaches of known methods, it turns out that a certain number of cycles is frequently missed before the prior art algorithms start to adapt to the new amplitude of the signal and are once again capable of detecting the cardiac rhythm correctly.

Figure 7C:
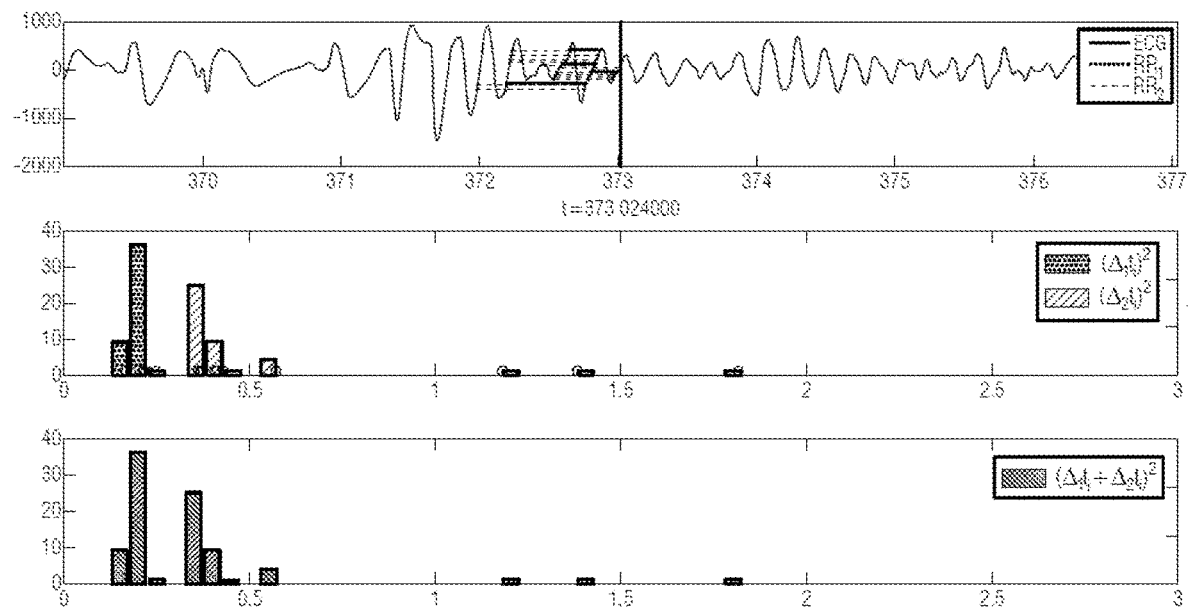
FIG. 7c represents a cardiac signal and corresponding histograms less than two seconds before the first cycle of a ventricular fibrillation episode.

The histogram of FIG. 7c is even more dispersed than that traced for the normal sinus rhythm (by comparison with FIG. 7a). The dispersion of the bars of the histogram of FIG. 7c indicates a turbulence in the cardiac rhythm. In addition, an offset towards the left of the bars of the histogram can be observed, i.e. an acceleration in the cardiac rhythm. The present method can thus be used to detect an acceleration in the cardiac rhythm just before the VF episode commences, i.e. before a first cardiac cycle during VF. The highest bar of the histogram of FIG. 7a is practically invisible in FIG. 7c.

Because of the presence of several threshold levels in accordance with the invention and in contrast to known prior art methods, the present method can be used to monitor the cardiac signal upon an approach to the VF episode even if the amplitude drops significantly. In fact, FIG. 7c illustrates the detection of a change in the amplitude of the signal over a time of approximately one second, between t=372 s and t=373 s, preceding the VF episode, by means of the plurality of threshold levels of the present method.

Thus, the present method can be used to improve detection of a transition towards a VF episode compared with known algorithms.

Figure 7D:
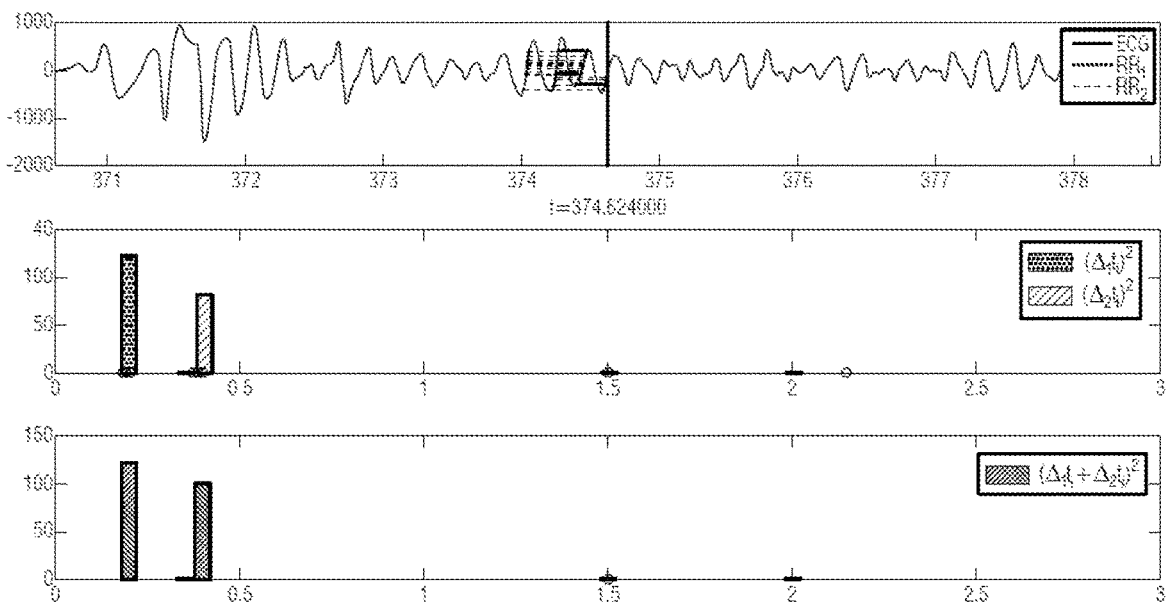
FIG. 7d represents a cardiac signal and corresponding histograms during a ventricular fibrillation episode.

FIG. 7d illustrates a cardiac signal during an episode of ventricular fibrillation. From the morphology of the signal in the form of wavelets, it will be observed that the amplitude of the signal is reduced during the VF episode compared with the amplitude of the cardiac signal preceding the VF episode, as can be seen in FIG. 7d by the amplitude of the signal before and after t=373. The histogram of FIG. 7d highlights a less dispersed distribution than that illustrated in FIG. 7c, but includes time intervals with values which are lower than those of FIG. 7a. In fact, the highest bar of FIG. 7d is centred on the value t=0.2 s.

Thus, with the present method, it is possible to observe a transition of the cardiac rhythm from a normal cardiac rhythm towards a VF episode by means of histograms, in particular by observing the dispersion and displacement of the bars constituting the histograms.

In accordance with one embodiment, the method may also comprise a step for receiving at least one cardiac signal via an implantable lead of an active implantable medical device which is configured in order to capture a cardiac signal subcutaneously.

Thus, the method is configured to process a cardiac signal which has been captured subcutaneously. The method is in fact suitable for processing a cardiac signal of this type for which all of the components are present, i.e. the QRS complex, the P wave and the T wave. For this reason, the method is configured for the determination of morphological and signal amplitude characteristics of a subcutaneously captured cardiac signal.

It should be noted that in the particular case in which the histogram, such as those shown in FIGS. 7a to 7d, comprises two bars with substantially equal heights and which are distinct from each other, linked together by the fact that each of the elapsed times $\Delta_2 t_i$ corresponds to twice the elapsed times $\Delta_1 t_i$, the present method is configured to select the time interval with the smaller value, i.e. the time interval corresponding to the elapsed times $\Delta_1 t_i$ for the determination of the statistical parameter.

In the case in which the histogram comprises two bars which are juxtaposed and which have substantially equal heights, for example because certain values for the elapsed times are at the border between one interval and another, the temporal analyses may be carried out by offsetting each bar of the histogram by half a period. In a variation, instead of representing the elapsed times by means of a histogram, a temporal distribution of the elapsed times may be considered. In this variation, the maxima of a time distribution curve for the elapsed times are determined and used for the determination of a statistical parameter.

The present invention also relates to a subcutaneous active implantable medical device comprising a housing, an implantable subcutaneous lead connected to the housing, the implantable subcutaneous lead comprising one or more sensing electrodes from which cardiac signals are captured subcutaneously. Said device furthermore comprises a control circuit configured to carry out the method in accordance with the present invention from at least one of the cardiac signals captured by the subcutaneous lead, in particular captured in real time. It should be noted that in a subcutaneous defibrillator, the cardiac signals detected by the subcutaneous lead are more like those of a standard surface electrocardiogram (ECG) in which all of the components (QRS complex, P and T waves) are present, as illustrated in FIGS. 2, 3 and 4a.

The control circuit for the device may comprise a microcontroller which in turn comprises a processor.

What is claimed is:

1. A method for processing a cardiac signal represented as a function of time, the method comprising:
providing a number n of different threshold levels $N_i$, with i=1 to n, and n being greater than or equal to three;
detecting, from a given time T and per threshold level $N_i$, at least two successive intersections of the cardiac signal with the different threshold levels $N_i$, considering a crossing per increasing and/or decreasing value of the cardiac signal with the threshold level $N_i$;
determining at least one statistical parameter for the cardiac signal from the at least two successive intersections of the cardiac signal with the at least three different threshold levels $N_i$, wherein determining the at least one statistical parameter comprises determining a period of the cardiac signal, and wherein the at least one statistical parameter is indicative of an arrhythamia; and
providing, based on the at least one statistical parameter, a defibrillation shock to a patient.

2. The method of claim 1, wherein:
detecting the at least two successive intersections of the cardiac signal with the threshold level $N_i$ further comprises determining, from the given time T and per threshold level $N_i$, at least one elapsed time $\Delta_1 t_i$, where i=1 to n, between the at least two successive intersections of the cardiac signal with the threshold level $N_i$; and
the at least one statistical parameter is determined in based on the at least one elapsed time $\Delta_1 t_i$.

3. The method of claim 2, wherein:
a first elapsed time $\Delta_1 t_i$ is determined per threshold level $N_i$ between two most recent successive intersections from the given time T;
a second elapsed time $\Delta_2 t_i$ is determined per threshold level $N_i$ between a most recent intersection and a third most recent intersection from the given time T; and
the at least one statistical parameter for the cardiac signal is determined by comparing the first elapsed time $\Delta_1 t_i$ with the second elapsed time $\Delta_2 t_i$.

4. The method of claim 3, wherein the period of the cardiac signal from the given time T is determined based on a distribution by a number of the elapsed times ($\Delta_1 t_i$; $\Delta_2 t_i$).

5. The method of claim 4, wherein the distribution by the number of the elapsed times ($\Delta_1 t_i$; $\Delta_2 t_i$) per defined time interval is represented via a histogram, and wherein the period of the cardiac signal from the given time T is determined from a mean or a median of the elapsed times ($\Delta_1 t_i$; $\Delta_2 t_i$) corresponding to a bar of the histogram that represents a largest number of occurrences of the elapsed times ($\Delta_1 t_i$; $\Delta_2 t_i$).

6. The method of claim 4, wherein the distribution by number of the elapsed times ($\Delta_1 t_i$; $\Delta_2 t_i$) per defined time interval is represented by means of a histogram and wherein the period of the cardiac signal from the given time T is determined from a mean or a median of the elapsed times ($\Delta_1 t_i$; $\Delta_2 t_i$) comprised in a defined time interval that is greater than a time interval corresponding to that of one bar of the histogram.

7. The method of claim 3, wherein only the elapsed times ($\Delta_1 t_i$; $\Delta_2 t_i$) for which a value crosses a predefined threshold are taken into account in the determination of the at least one statistical parameter.

8. The method of claim 7, wherein the predefined threshold is determined from the detection of the at least two successive intersections of the cardiac signal with the threshold level $N_i$, at a time before the given time T.

9. The method of claim 1, wherein providing the number n of different threshold levels $N_i$ comprises determining a minimum amplitude and a maximum amplitude of the cardiac signal, such that values for the different threshold levels $N_i$ are determined so that they are between a minimum value and a maximum value respectively corresponding to the minimum amplitude and the maximum amplitude of the cardiac signal.

10. The method of claim 1, wherein a value for each of the different threshold levels $N_i$ is constant over time.

11. The method of claim 1, wherein a value for the different threshold levels $N_i$ varies over time as a function of the at least one statistical parameter.

12. The method of claim 1, wherein each of the different threshold levels $N_i$ are spaced apart by a fixed interval.

13. The method of claim 1, wherein providing a number n of different threshold levels $N_i$ comprises providing at least ten different threshold levels $N_i$.

14. The method of claim 1, wherein each of the different threshold levels $N_i$ is different from a base line.

15. The method of claim 1, wherein the cardiac signal is captured via an implantable lead of an active implantable medical device configured to capture cardiac signals subcutaneously.

16. The method of claim 1, further comprising determining an interval between crossings of two successive threshold levels $N_{i=n}$ and $N_{i=n+1}$ by the cardiac signal.

17. A subcutaneous active implantable medical device comprising:
a housing;
a subcutaneous implantable lead connected to the housing and comprising one or more sensing electrodes configured to capture cardiac rhythms subcutaneously; and
a control circuit configured to:
provide a number n of different threshold levels $N_i$, with i=1 to n, and n being greater than or equal to three;
detect, from a given time T and for each of the different threshold levels $N_i$, at least two successive intersections of a cardiac signal with each of the different threshold levels $N_i$, wherein each of the at least two successive intersections indicate to a crossing of a threshold level $N_i$ due to an increasing or decreasing value of the cardiac signal;
determine at least one statistical parameter for the cardiac signal from the at least two successive intersections of the cardiac signal with the different threshold levels $N_i$, wherein the determination of the at least one statistical parameter comprises determining a period of the cardiac signal, and wherein the at least one statistical parameter is indicative of an arrhythmia; and
provide, based on the at least one statistical parameter, a defibrillation shock to a patient.

18. The device of claim 17, wherein:
detecting the at least two successive intersections of the cardiac signal with the threshold level $N_i$ further comprises determining, from the given time T and for a particular threshold level $N_i$, at least one elapsed time $\Delta_1 t_i$, where i=1 to n, between the at least two successive intersections of the cardiac signal with the particular threshold level $N_i$; and
the at least one statistical parameter is determined in based on the at least one elapsed time $\Delta_1 t_i$.

* * * * *